(12) United States Patent
Roeder

(10) Patent No.: US 8,753,889 B1
(45) Date of Patent: Jun. 17, 2014

(54) METHODS FOR DIAGNOSING AND TREATING DISEASE IN ANIMALS BY THE ANALYSIS OF ISOTOPES IN ELEMENTS SUCH AS CARBON AND NITROGEN IN ANIMAL SUBSTRATE

(76) Inventor: Beverly L. Roeder, Sandy, UT (US)

( * ) Notice: Subject to any disclaimer, the term of this patent is extended or adjusted under 35 U.S.C. 154(b) by 311 days.

(21) Appl. No.: 13/078,027

(22) Filed: Apr. 1, 2011

Related U.S. Application Data

(60) Provisional application No. 61/341,565, filed on Apr. 1, 2010.

(51) Int. Cl.
*G01N 33/50* (2006.01)

(52) U.S. Cl.
USPC .............................. 436/56; 436/173; 424/1.65

(58) Field of Classification Search
USPC .............................. 436/804, 56, 173; 424/1.65
See application file for complete search history.

(56) References Cited

U.S. PATENT DOCUMENTS

| | | | |
|---|---|---|---|
| 4,068,122 | A | 1/1978 | Schmidt |
| 5,912,178 | A | 6/1999 | Porter |
| 7,465,276 | B2 * | 12/2008 | Assadi-Porter et al. ...... 600/532 |

FOREIGN PATENT DOCUMENTS

| | | | |
|---|---|---|---|
| EP | 1006198 A1 | * | 6/2000 |
| WO | WO 2007054940 A2 | * | 5/2007 |

OTHER PUBLICATIONS

Ivashkin et al., "Laser analysis of carbon isotope ratio 13C/12C in exhaled air in diagnostics and treatment of H. pylori-associated diseases," Trudy Instituta Obshchei Fiziki imeni A. M. Prokhorova, Rossiiskaya Akademiya Nauk 61:253-277, 2005, abstract only.*
Parra et al., "Methodological characterization of the 2-keto [1-13C] isocaproate breath test to measure in vivo human mitochondrial function: application in alcoholic liver disease assessment," Alcoholism: clinical and experimental research 27(8):1293-1298, 2003, abstract only.*
Boedeker et al., "13C mixed triglyceride breath test: isotope selective non-dispersive infrared spectrometry in comparison with isotope ratio mass spectrometry in volunteers and patients with chronic pancreatitis," Scandinavian Journal of Gastroenterology 34(11):1153-1156, 1999, abstract only.*
Leblanc, S.J. Metabolic Predictors of Displaced Abomasum in Dairy Cattle. J Dairy Sci 2005 88(1), 159-170.
Musshoff, F. Analytical Pitfalls in Hair Testing. Anal Bioanal Chem 2007 388(7), 1475-1494.
O'Connel, T.C. Investigation Into the Effect of Diet on Modern Human Hair Isotopic Values. Am J Phys Anthropol 1999 108(4), 409-425.
Petzke, K.J. Carbon and Nitrogen Stable Isotopic Composition of Hair Protein and Amino Acids Can Be Used as Biomarkers for Animal-Derived Dietary Protein Intake in Humans. J Nutr 2005 135(6), 1515-1520.
Petzke, K.J. Advances in Natural Stable Isotope Ratio Analysis of Human Hair to Determine Nutritional and Metabolic Status. Curr Opin Clin Nutr Metab Care 2010 13(5), 532-540.
Reist, M. Use of Threshold Serum and Milk Ketone Concentrations to Identify Risk for Ketosis and Endometritis in High-Yielding Dairy Cows. Am J Vet Res 2003 64(2), 188-194.

* cited by examiner

*Primary Examiner* — Rosanne Kosson
(74) *Attorney, Agent, or Firm* — Kunzler Law Group

(57) ABSTRACT

Methods are disclosed for using stable isotopes of carbon and nitrogen in hair and feces to predict disease in animals such as predicting the susceptibility of dairy cows to periparturient production-related metabolic diseases (PRMDs). Other methods that are disclosed are for using stable isotopes of carbon and nitrogen in blood components, erythrocytes and plasma proteins, to predict dairy cow susceptibility to PRMDS; yet other disclosed methods are for using stable isotopes of carbon and nitrogen in hair and feces of horses as a prognostic indicator after surgical or medical correction of gastrointestinal colic. Other methods that are disclosed also include using stable isotopes of carbon and nitrogen in blood components, erythrocytes and plasma proteins, of horses as a prognostic indicator before or after surgical or medical correction of gastrointestinal colic.

10 Claims, No Drawings

METHODS FOR DIAGNOSING AND TREATING DISEASE IN ANIMALS BY THE ANALYSIS OF ISOTOPES IN ELEMENTS SUCH AS CARBON AND NITROGEN IN ANIMAL SUBSTRATE

No federal grant money was used to support the research that contributed to the invention.

BACKGROUND OF THE INVENTION

Periparturient production-related metabolic diseases (PRMDs) occur in dairy cows near the time of parturition, which is the time when a cow gives birth. Some examples of factors that are related to PRMDs are: fatty liver, ketosis, mastitis, and displaced abomasums, with or without concurrent illness associated with an infection. Cows are most susceptible to these PRMDs during the rapid increase in milk secretion at the time of parturition, which causes a decrease in blood glucose and insulin concentrations. However, increased energy demand of later fetal growth and lactogenesis cause compensatory prepartum serum non-sterified fatty acids (NEFA) release. PRMDs can cause decreased milk yield, medication costs, and increased culling, or removal, of animals. In the past, efforts have been devoted to identify when most PRMDs occur and to institute management practices to help decrease the incidence of PRMDs in dairy cows. Although progress has been made in understanding the biology of energy metabolism and immune function in transition cows, formulating transition diets, dietary cation-anion difference (CAD), avoiding over-conditioning, and identifying when most PRMDs occur, the incidence of PRMDs has remained stable. Some efforts have included measuring levels of various chemicals in a cow's blood. Correlations have been found linking risk of PRMDs with serum concentrations of free fatty acids (FFAs), NEFAs, triglycerides (TG), beta-hydroxybutyrate (BHBA), as well as hepatic TG to glycogen ratios. Serum concentration of NEFA taken one week before parturition and milk concentration of BHBA taken one week after parturition have been linked to risk of displaced abomasum (LeBlanc, Leslie, & Duffield, 2005). Risk of ketosis and endometritis has been linked to levels of ketones in milk and blood above a certain threshold at one week after parturition (Reist, Erdin, Euw, Tschümperlin, Leuenberger, Hammon, et al., 2003). One study found that levels of vitamin C in plasma were not related to risk of ketosis (Padilla, Shibano, Inoue, Matsui, & Yano, 2005). Previous methods to predict risk of developing PRMDs using many of the relationships found involves an average cost for this battery of tests at approximately $30-50/sample with a requisite submission of 11 or more samples, necessitating an increased expense of obtaining blood from groups of cows to predict herd risk. Also, many of the relationships require waiting for testing until after parturition, when the onset of disease is approaching.

A need, therefore, exists for a method to accurately predict individual cow risk of PRMDs using a minimally or noninvasive procedure that can be performed at or before parturition. It would be desirable to predict risk of PRMDs early to allow for early intervention that would reduce the loss in milk production, cost of medication, and culling of animals.

It has been shown that the ratios of certain isotopes in an organism's tissues are related to the organism's metabolism. Recent studies of stable isotope ratios (2H/1H, 13C/12C, 15N/14N, 18O/16O, and 34S/32S) have yielded information about "dietary habits and the metabolic status of prehistoric and modern humans, eating disorders, forensic medicine, geographical location, and wildlife dietary ecology" (see Petzke, Fuller, & Metges, 2010). Every food source in an animal's diet contains certain ratios of isotopes, such as the ratio of carbon-13 (13C) to carbon-12 (12C). Often these ratios will be different in the animal's tissues due to a process called isotopic fractionation. Isotopic fractionation refers to the alteration of isotope levels as a result of chemical or physical processes. For example, some metabolic processes discriminate against the heavier 13C isotope, and therefore molecules containing the 13C isotope are not metabolized as readily as molecules containing only the 12C isotope. When the animal's body metabolizes energy sources such as lipids and proteins, the level of 13C in the animal's tissue becomes enriched because the body tends to metabolize more lipids and proteins containing 12C, and less containing 13C. In addition to affecting isotope levels in tissue, metabolic processes can affect isotope levels in metabolic byproducts, such as feces, and metabolically-inert substrates, such as hair. Studies examining stable isotopes at or near natural abundance levels are usually reported as delta (δ), a value given in parts per thousand or per mil ("o/oo"). Delta values are not absolute isotope abundances but differences between sample readings and one or another of the widely used natural abundance standards which are considered delta=zero (e.g. air for N, At %15N=0.3663033; Pee Dee Belemnite for C, At %13C=1.1112328). Absolute isotope ratios (R) are measured for sample and standard, and the relative measure delta is calculated:

$$\delta^{15}N \ o/oo \ \text{vs.} \ [\text{std}] = ((R\text{sample} - R\text{std})/R\text{std})(1000 \delta o/oo)$$

where $$R = (\text{At } \%^{15}N)/\text{At } \%^{14}N)$$

For instance, if a leaf sample is found to have a 15N/14N ratio R greater than the standard's by 5 parts per thousand, this value is reported as δ15N=+5 delta o/oo. The transformation of absolute At % values into relative (to a certain standard) delta values is used because the absolute differences between samples and standard are quite small at natural abundance levels and might appear only in the third or fourth decimal place if At % were reported." (See http://www.uga.edu/sisbl/stable.html, accessed on 30 Mar. 2011).

Ratios of isotopes, such as the ratio of 13C to 12C, are sometimes referred to as isotopic "signatures." These signatures can differ between individual animals even when the animals consume identical diets. The differences are related to nutrient assimilation, which is regulated by innate metabolism. Differences in innate metabolism may be influenced by an individual animal's genetics. Some animal substrates are metabolically active, meaning that they are constantly being reformed through metabolic processes. These substrates include by-products of metabolism such as breath, urine, and feces. The isotopic signatures in these substrates are constantly changing as they are continuously produced by metabolic processes. Other metabolically active substrates are replaced at particular time intervals, such as erythrocytes, which are replaced approximately every three months, or plasma proteins, which are replaced approximately every two weeks. The isotopic signatures of these substrates are affected by metabolic processes occurring throughout the time interval since they were formed. Metabolically inert substrates include hair, fur, hooves, claws, feathers, and other tissues that do not change after they are formed. These substrates retain the isotopic signatures present at their formation, and so they can provide a historical record relating to the animal's metabolism. For example, every point along a strand of hair may have slightly different isotopic signatures because of changes that occurred in the animal's metabolism while the hair was growing. After the proteins making up the strand of hair are formed, they are never replaced or otherwise affected by metabolic processes, so they retain the same isotopic signature as they had at formation.

Isotopic signatures have been used to learn about the diet of humans and animals. Isotopes in hair of ancient human remains have allowed reconstruction of dietary conditions in ancient human populations (Petzke, Fuller, & Metges, 2010). It has been found that isotope signatures in hair of modern humans are related to excessive intake of meat products (Petzke, Boeing, Klaus, & Metges, 2005). This relationship has potential to be used to correct errors in studies requiring self-reporting of meat intake, because it provides an objective standard against which to check self-reporting.

It would be desirable to provide a method of using isotopic signatures to predict PRMDs in dairy cows which would be accurate, noninvasive, and performable at or before parturition to allow time for early intervention.

Horses treated for gastrointestinal colic sometimes die or continue to have health problems after treatment. It would be desirable to provide a method for predicting the likelihood of continued health problems in order to decide what treatment options would best enhance recovery or to relieve unavoidable pain and suffering with early humane euthanasia.

BRIEF SUMMARY OF THE INVENTION

This document describes methods for predicting diseases in animals, detecting disease in animals, and predicting a poor outcome of a medical intervention for a disease in an animal. The methods relates to using isotopic analysis to predict diseases in animals. Methods are disclosed for predicting production-related metabolic diseases (PRMDs) in animals such as dairy cows. Methods are disclosed for using isotopic analysis to predict prognosis outcomes for horses following treatment of gastrointestinal colic.

Some of the disclosed methods relate to detecting or predicting the presence of at least one disease in an animal, and some of the methods include steps such as collecting from the animal one or more samples hair, feces, blood, erythrocytes, plasma or proteins; measuring the amount of a first isotope in said sample and the amount of a second isotope in said sample; determining an isotopic signature for a stable isotope by submethods such as determining a first ratio between said amount of said first isotope and said amount of said second isotope; collecting from said animal a second at least one sample of animal substrate selected from the group consisting of a sample of hair, a sample of feces, a sample of blood, a sample of erythrocytes, a sample of plasma proteins, and any combination thereof; measuring the amount of a third isotope in said sample and the amount of a fourth isotope in said sample; determining a second ratio between said amount of said third isotope and said amount of said fourth isotope; and, determining if a statistically significant difference exists 1) between said first ratio and a first set of reference numbers from reference samples and 2) between said second ratio and a second set of reference numbers from reference samples, and if so, then predicting that said warm-blooded animal has an increased risk of developing said disease; and, treating said animal for said disease. Some of the disclosed methods relate to warm-blooded animals and the measurement of isotopes such as $^{15}N$, $^{14}N$, $^{13}C$, and $^{12}C$. Some of the disclosed methods relate to diagnosing or predicting disease in animals that have not yet displayed visually-discernible symptoms of said disease. Some of the methods contemplate diseases such as a periparturient production-related metabolic disease. Some of the methods contemplate collecting animal substrate from animals during various developmental stages, such as the prepartum stage, a partition stage, or a postpartum stage. Some of the methods relate to collecting feces during all of the collections of animal substrate; some other methods relate to collecting feces or hair during all of the collections of animal substrate; yet other disclosed methods relate to dairy cows. Some of the disclosed methods relate to performing analysis of ratios of stable isotopes in animals by comparing the ratios of stable isotopes contained in animal substrate to reference samples taken from a control group or a reference group and then based on correlations or the results of the statistical analysis treating the animal, culling the animal, euthanizing the animal, performing a specific treatment on the animal, or monitoring the animal before treating the animal. Some of the disclosed methods relate to collecting samples of animal substrate and then in any order freezing the sample, freeze-drying the sample, grinding the sample, homogenizing the sample. Some of the disclosed methods relate to performing statistical analysis on isotopes isolated from animal substrate and based on the results of the statistical analysis treating the animal immediately, within 24 hours, or within longer periods of time than 24 hours. Some of the disclosed methods relate to predicting whether a horse will respond well to a medical intervention (which includes surgical intervention) to correct gastrointestinal colic and euthanizing the horse if the results of the statistical analysis on the horse's substrate indicates a decreased likelihood or low likelihood that the horse will stop exhibiting symptoms of gastrointestinal colic after medical intervention. Some of the methods contemplate collecting samples of animal substrate from an animal on the same day, different days, or on days with intervals of greater than one week; some of the methods contemplate taking four or more samples from the same animal; other methods contemplating taking less than four samples; some methods contemplate determining the isotopic signature of $^{15}N$ and the isotopic signature of $^{13}C$ from the same sample, such as collecting a sample of feces or hair and then determining an isotopic signature of $^{15}N$ from a portion of the hair or feces and determining the isotopic signature of $^{13}C$ from a different portion of the hair or feces. Other methods contemplate determining different isotopic signatures from different samples of animal substrate.

DETAILED DESCRIPTION OF THE INVENTION

Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents such as U.S. Pat. No. 5,912,178, patent applications, articles, books, and treatises, are hereby expressly incorporated by reference in their entirety for any purpose. Unless otherwise specified, the steps of a method may be conducted in any order.

Animal substrates and metabolic by-products differ in their carbon and nitrogen isotopes. Lipid fractions have a more depleted $^{13}C/^{12}C$ ratio ($\delta^{13}C$) than protein and carbohydrate fractions. Hair $\delta^{13}C$ values reflect the C isotope composition of dietary protein, rather than the formation. However, if endogenous lipid and protein stores are mobilized for energy, the $\delta^{13}C$ values in substrates should become more depleted, and $^{15}N/^{14}N$ ratios ($\delta^{15}N$) should become more enriched.

In many metabolic processes of animal bodies the heavier isotope is discriminated against, and the heavier isotope tends to remain in the organism, which leads isotopically enriched differences (that is, "enrichment") that are related to nutrient assimilation and incorporation regulated by innate metabolism. Differences between animals in metabolisms of heavier isotopes may be influenced by an organism's genetics, which may cause subtle differences in the isotopic signatures of $^{13}C/^{12}C$ and $^{15}N/^{14}N$ to be integrated into metabolic by-products and/or metabolically inert substrates.

Predictions of likelihood of PRMD or prognostic indication of recovery from GIT colic may be based on different isotopic signatures or abundances of C and N in different or the same type of substrates collected at the same time, and other tissues of animals of the same species, consuming the same diet in lesser, the same, or increased amounts, that meet or exceed the need for maintenance or production (i.e. growth and/or reproduction and/or lactation), that may or may not go on to develop PRMDs.

As used herein, animal substrates refers to: hair, blood components such as erythrocyte and plasma fractions, feces, hoof keratin, and any animal tissue or waste product from an animal's metabolism.

As used herein, assimilation refers to the process in which nutrients that were ingested were absorbed and integrated or incorporated into building the animal's tissues like hair, erythrocytes, plasma protein, gastrointestinal tract ("GIT") cells, and so forth—the nutrients did not pass through the GIT without absorption).

As used herein, disease is interpreted broadly to include heart failure, inability to be weaned at the normal developmental stage, inability to walk at the normal developmental stage, and includes but is not limited to gastrointestinal colic, recurrent airway obstruction, laminitis, hoof problems, inability to recover from treatment for parasites, exertional rhabdomyolysis, lameness, mastitis, retained placenta, endometritis, cystic ovaries, ketosis, milk fever, hypomagnesemia, and periparturient production-related metabolic diseases.

As used herein, medical intervention or medical treatment is to be interpreted broadly to also include surgical treatment or surgical intervention.

As used herein an isotopic signature is broadly interpreted as a ratio of stable or unstable isotopes of particular elements found in an investigated material.

This document discloses methods that uses stable isotopes of $^{13}C/^{12}C$ and 15N/14N in feces, erythrocytes, plasma proteins, and/or hair from a single sampling time prepartum or at parturition as previously determined by discriminant analysis or comparison samples that are from temporally and isotopically different pairs of isotopes, that can provide a method to predict the likelihood that a clinically normal cow will later develop periparturient (2 wks pre- to 16 wks post-partum) production-related metabolic disease(s) (PRMDs). The prediction uses either a single sample time or two or more temporally different periods, where carbon and nitrogen isotopic signature pairs present in the same sample type or in another type of specimen from the animal are determined. If the values of these different isotopic pairs from single time, contemporaneous samples or from non-contemporaneous, similar or different samples from an animal, are above or below a reference range, then a user of the method can predict that the animal has PRMDs or has an increased risk of developing PRMDs.

Similarly, both $\delta^{13}C$ and $\delta^{15}N$ isotopic signatures in biological substrates are measured to predict recovery or survival outcome for equids suffering from GIT colic that receive medical or surgical intervention. Additionally, the methods disclosed in the document can be used to predict recovery or survival outcome in equids that are suffering from GIT colic even before medical or surgical intervention have been administered.

In some embodiments, stable isotopes such as $^{13}C/^{12}C$ and $^{15}N/^{14}N$ are obtained from animals in a single draw or on multiple draws. Multiple draws may be at regular time intervals, such as daily.

Materials and Methods

Randomly chosen, age, lactation, and parity matched primiparous and multiparous Holstein cows, Brigham Creek Dairy (Elberta, Utah) were studied. Hair and feces were sampled 21 days prepartum (P1), at parturition (P2), and 21 days postpartum (P3). Cow weekly milk production (MP) was recorded. Feces samples were frozen, freeze-dried, ground and homogenized. Hair samples were cleaned via sonication. Samples of feces and mm lengths of hair (range of 0.3 to 0.6 mg) were weighed in tin capsules with a microbalance for analysis of % C, % N, $\delta^{13}C$, $^{15}N$, and C:N ratios. Combusted samples were analyzed in duplicate using an elemental analyzer coupled to a DeltaV isotope ratio mass spectrometer to isolate C and N for $\delta^{15}N$ and $\delta^{13}C$ analysis by atomic weight. All ratios were expressed in parts per mil (‰) relative to C and N standards Pee Dee Belemnite and atmospheric nitrogen, respectively. Samples were corrected using external standards for carbon UCLA Carrera and LSVEC, and nitrogen USGS 25 and 26. Raw data from substrate sample results were calibrated against $\delta^{13}C$ and $\delta^{15}N$ values obtained from known internal and/or external (obtained from Intl Atomic Energy Agency=IAEA or United States Geological Survey=USGS) standards that were analyzed simultaneously with the unknowns). Health score (HSC) ranking: Clinically normal cows were scored as HSC=1 (healthy, adequate milk production ("MP")). Cows that became ill with a PRMD, but later recovered, and had adequate milk production that lactation were scored HSC 2 (illness, recovery, adequate MP). Cows that had poor milk production associated with or without a diagnosed PRMD were scored HSC 3 (culled poor MP+/−PRMD). Cows that succumbed to a PRMD and died were scored HSC 4 (died). Cows that were either culled from the herd or died within one to five months after parturition were scored HSC 5 (culled/died+/−PRMD 1-5 months postpartum). Data were analyzed using Statistical Analysis Software (SAS). Discriminant analysis, grouping variable HSC, was performed for each pre- and postpartum hair and feces measure. The statistical analysis used a general linear model procedure, with the independent variable HSC, and determined if isotopic measures in hair and feces were different when compared to reference samples for clinically normal cows that scored HSC 1 than cows that were scored with HSC 3, 4, 5. Significance level of $p<0.05$ for all tests.

Reference numbers and control ratios from reference samples were derived from empirical studies with cows and heifers, indicating that those animals with more isotopically enriched P1 $\delta^{13}C$ feces and P2 $\delta^{15}N$ feces, compared to animals that remained healthy in the subsequent lactation, were accurately predicted 75% of the time to be at risk for development of PRMDs. In some embodiments, $\delta^{15}N$ and $\delta^{13}C$ isotopic signatures, as well as isotopic signatures for other elements, are calculated from samples of animal substrate from a control group of animals; the HSCs for the animals are tracked and compared with their isotopic signatures to determine control ratios.

Results

The interaction of HSC and P3 weekly average lactation was not well correlated with $\delta^{15}N$ and $\delta^{13}C$ isotopic signatures in hair. Mean $\delta^{15}N$ and $\delta^{13}C$ values in hair were less predictive of HSC. In order, the best predictor of HSC during and after the transition period was P2 feces $\delta^{13}C$ and P1 feces $\delta^{15}N$. These parameters correctly predicted 75% of cows with HSC 3, and all with HSC 4 and 5. HSC 1 cows were correctly classified 58% of the time, but incorrectly classified 21%, 7%, and 1% as HSC 3, 4, and 5, respectively.

Analysis of Hair:

Serial sectioning and separate analyses of hair collected at one sampling may yield temporal isotopic signatures and abundances that could be predictive of PRMD risk.

Methods for Monitoring Dairy Cows that have Isotopic Ratios that Correlate with Disease Dairy cattle predicted to be at high risk for PRMDs may be observed; examples of observable data are: daily for milk production quantity, body temperature measurement, appetite, and urine ketone measurement. Any discrepancies in observable data and observable data from normal dairy cattle should dictate interventional preventive therapy, including nutritional, antimicrobial, and/or supportive measures.

Methods for Testing Equid Biological Substrates and for Interpreting the Results In some embodiments stable isotopes of $^{13}C/^{12}C$ and $^{15}N/^{14}N$ in contemporaneous, single time samples of feces, erythrocytes, plasma proteins, and/or hair obtained from horses may be used as a prognostic indicator of outcome after surgical or medical correction of gastrointestinal colic. This inference is based on the premise that differences in nutrient assimilation and isotopic fractionation patterns in equines from innate metabolism differences, that may be genetic in origin, may provide a method to predict a horse's prognosis for outcome after surgical or medical correction of gastrointestinal colic.

In some embodiments, biological substrates are obtained from an equid being evaluated for GIT colic to determine differences in stable carbon ($\delta^{13}C$) and nitrogen ($\delta^{15}N$) isotope ratios and relative abundances. Nonlimiting examples of biological substrates are hair, blood sample separated into erythrocyte and plasma fractions, and feces. In some embodiments, discriminant analysis of substrate isotopic signature and relative abundance results from a reference population of equids whose substrates were previously analyzed are used to determine which values and range of values are most predictive of: survival, continued health problems related to GIT colic, or death for an effected equid. In cases of equid GIT colic, test results may be used as an economical decision making tool to determine what treatment option(s) are best to enhance recovery or whether early humane euthanasia would relieve irreversible pain and suffering.

It should be appreciated that the compositions and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention, therefore, indicated by the appended claims rather than by the foregoing description. All changes which come within the meaning and range of equivalency of the claims are to be embraced within their scope.

CITATIONS

Porter et al. U.S. Pat. No. 5,912,178.
Assadi-Porter et al. U.S. Pat. No. 7,465,276.
Schmidt et al. U.S. Pat. No. 4,068,122
LEBLANC, S. J. Metabolic Predictors of Displaced Abomasum in Dairy Cattle. J Dairy Sci 2005 88(1), 159-170.
MUSSHOFF, F. Analytical Pitfalls in Hair Testing. Anal Bioanal Chem 2007 388(7), 1475-1494.
O'CONNEL, T. C. Investigation Into the Effect of Diet on Modern Human Hair Isotopic Values. Am J Phys Anthropol 1999 108(4), 409-425.
PADILLA, L. Plasma Vitamin C Concentration is Not Related to the Incidence of Ketosis in Dairy Cows During the Early Lactation Period. J Vet Med Sci 2005 67(9), 883-886.
PETZKE, K. J. Carbon and Nitrogen Stable Isotopic Composition of Hair Protein and Amino Acids Can Be Used as Biomarkers for Animal-Derived Dietary Protein Intake in Humans. J Nutr 2005 135(6), 1515-1520.
PETZKE, K. J. Advances in Natural Stable Isotope Ratio Analysis of Human Hair to Determine Nutritional and Metabolic Status. Curr Opin Clin Nutr Metab Care 2010 13(5), 532-540.
REIST, M. Use of Threshold Serum and Milk Ketone Concentrations to Identify Risk for Ketosis and Endometritis in High-Yielding Dairy Cows. Am J Vet Res 2003 64(2), 188-194.

What is claimed is:

1. A method of detecting or predicting the presence of at least one production related metabolic disease (PRMD) in a test animal comprising:
   (a) collecting from the test animal at least one first sample of animal substrate comprising at least one of hair, feces, blood, erythrocytes, plasma protein, and any combination thereof;
   (b) measuring the amount of a first isotope in the first sample and the amount of a second isotope of the same element in the first sample;
   (c) determining a first ratio between the amount of the first isotope and the amount of the second isotope of the same element in the first sample;
   (d) collecting from the test animal a second at least one sample of animal substrate- comprising at least one of hair, feces, blood, erythrocytes, plasma protein, and any combination thereof;
   (e) measuring the amount of a third isotope in the second sample and the amount of a fourth isotope of the same element in the second sample;
   (f) determining a second ratio between the amount of the third isotope and the amount of the fourth isotope in the second sample;
   (g) comparing the test animal first ratio with a first control ratio of the first and second isotopes from a healthy animal other than the test animal and comparing the test animal second ratio with a second control ratio of the third and fourth isotopes from a healthy animal other than the test animal;
   (h) determining if a statistically significant difference exists between the test animal first ratio and first control ratio and between the test animal second ratio and the second control ratio; and if so,
   (i) determining that the test animal has the PRMD or predicting that the test animal is at risk of developing the PRMD, wherein the PRMD is selected from the group consisting of milk fever, ketosis, retained placenta, endometritis, fatty liver, mastitis, displaced abomasum, gastrointestinal colic, recurrent airway obstruction, laminitis, inability to recover from treatment for parasites, exertional rhabdomyolysis, lameness, cystic ovaries, hypomagnesemia, and a periparturient production-related metabolic disease (PPRMD).

2. The method of claim 1 wherein the animal is a warm-blooded animal, and wherein the first isotope is $^{15}N$, the second isotope is $^{14}N$, the third isotope is $^{13}C$, and the fourth isotope is $^{12}C$.

3. The method of claim 2 wherein the warm-blooded animal does not display visually-discernible symptoms of the disease, and wherein the disease is a periparturient production-related metabolic disease (PPRMD).

4. The method of claim 3 wherein the first at least one sample is collected during a prepartum stage of the test animal and wherein the second at least one sample is collected during a parturition stage of the test animal.

5. The method of claim 4 wherein the first at least one sample of animal substrate is feces and the second at least one sample of animal substrate is feces.

6. The method of claim 5 wherein the test animal is a dairy cow.

7. The method of claim 6 further comprising monitoring a test animal predicted for increased risk of disease and culling the test animal if disease develops.

8. The method of claim 7, wherein the step of collecting from the test animal a first at least one sample consists of freezing the sample of feces, freeze-drying the sample of feces, grinding the sample of feces, and homogenizing the sample of feces, and wherein the step of collecting from the test animal a second at least one sample consists of freezing the sample of feces, freeze-drying the sample of feces, grinding the sample of feces, and homogenizing the sample of feces.

9. The method of claim 6 further comprising monitoring the test animal for symptoms of the PRMD and instituting treatment intervention on behalf of the test animal exhibiting symptoms of the disease.

10. The method of claim 9 wherein the step of treating the test animal for the clinical signs of the disease occurs within the 24 hour period following the test animal exhibiting the clinical signs of the disease.

* * * * *